United States Patent
Schwartz et al.

(10) Patent No.: US 7,539,536 B2
(45) Date of Patent: *May 26, 2009

(54) CARDIAC RHYTHM MANAGEMENT SYSTEMS AND METHODS USING MULTIPLE MORPHOLOGY TEMPLATES FOR DISCRIMINATING BETWEEN RHYTHMS

(75) Inventors: Mark Schwartz, Hugo, MN (US);
Joseph M. Bocek, Seattle, WA (US);
Jaeho Kim, Redmond, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 438 days.

This patent is subject to a terminal disclaimer.

(21) Appl. No.: 11/277,095

(22) Filed: Mar. 21, 2006

(65) Prior Publication Data

US 2006/0155201 A1    Jul. 13, 2006

Related U.S. Application Data

(63) Continuation of application No. 10/291,200, filed on Nov. 8, 2002, now Pat. No. 7,031,764.

(51) Int. Cl.
*A61B 5/0464* (2006.01)
*A61N 1/365* (2006.01)

(52) U.S. Cl. .................. 600/518; 600/509; 600/515

(58) Field of Classification Search .......... 600/508, 600/509, 515–518, 510; 607/4, 5, 9, 14, 607/28

See application file for complete search history.

(56) References Cited

U.S. PATENT DOCUMENTS

| | | | |
|---|---|---|---|
| 4,023,564 A | | 5/1977 | Valiquette et al. |
| 4,336,810 A | | 6/1982 | Anderson et al. |
| 4,407,288 A | * | 10/1983 | Langer et al. ............. 607/4 |
| 4,452,248 A | * | 6/1984 | Keller, Jr. .................. 607/9 |
| 4,589,420 A | | 5/1986 | Adams et al. |
| 4,680,708 A | | 7/1987 | Ambos et al. |

(Continued)

FOREIGN PATENT DOCUMENTS

DE    4405827    6/1995

(Continued)

OTHER PUBLICATIONS

Horowitz et al. "Epicardial and endocardial activation during sustained ventricular tachycardia in man." Circulation. 1980; vol. 61, No. 6; 1227-1238.*

(Continued)

*Primary Examiner*—Carl H Layno
*Assistant Examiner*—Luther G Behringer
(74) *Attorney, Agent, or Firm*—Schwegman, Lundberg & Woessner, P.A.

(57) ABSTRACT

This document describes systems, devices, and methods that use multiple morphology templates for discriminating between rhythms, such as supraventricular tachyarrhythmias (SVTs) and ventricular tachyarrhythmias (VTs), for delivering a countershock in response to a VT episode, but withholding delivery of such a countershock in response to an SVT episode. In certain examples, the particular morphology used for storing morphological features is selected at least in part using a sensor-indicated activity level of a subject, or a metabolic need of the subject.

21 Claims, 10 Drawing Sheets

U.S. PATENT DOCUMENTS

| | | | |
|---|---|---|---|
| 4,721,114 A | 1/1988 | DuFault et al. | |
| 4,802,491 A | 2/1989 | Cohen et al. | |
| 4,809,697 A | 3/1989 | Causey, III et al. | |
| 4,825,869 A | 5/1989 | Sasmor et al. | |
| 4,830,006 A | 5/1989 | Haluska et al. | |
| 4,884,345 A | 12/1989 | Long | |
| 4,940,054 A | 7/1990 | Grevis et al. | |
| 4,947,857 A | 8/1990 | Albert et al. | |
| 4,989,610 A | 2/1991 | Patton et al. | |
| 5,000,189 A * | 3/1991 | Throne et al. | 600/515 |
| 5,010,888 A * | 4/1991 | Jadvar et al. | 600/509 |
| 5,014,698 A | 5/1991 | Cohen | |
| 5,020,540 A | 6/1991 | Cahmoun | |
| 5,046,504 A | 9/1991 | Albert et al. | |
| 5,047,930 A | 9/1991 | Martens et al. | |
| 5,092,341 A | 3/1992 | Kelen | |
| 5,183,040 A | 2/1993 | Nappholz et al. | |
| 5,184,615 A | 2/1993 | Nappholz et al. | |
| 5,193,535 A | 3/1993 | Bardy et al. | |
| 5,193,550 A | 3/1993 | Duffin | |
| 5,215,098 A | 6/1993 | Steinhaus et al. | |
| 5,217,021 A | 6/1993 | Steinhaus et al. | |
| 5,240,009 A | 8/1993 | Williams | |
| 5,269,301 A | 12/1993 | Cohen | |
| 5,271,411 A | 12/1993 | Ripley et al. | |
| 5,273,049 A | 12/1993 | Steinhaus et al. | |
| 5,280,792 A | 1/1994 | Leong et al. | |
| 5,292,348 A | 3/1994 | Saumarez et al. | |
| 5,299,118 A | 3/1994 | Martens et al. | |
| 5,311,873 A | 5/1994 | Savard et al. | |
| 5,311,874 A | 5/1994 | Baumann et al. | |
| 5,312,445 A | 5/1994 | Nappholz et al. | |
| 5,313,953 A | 5/1994 | Yomtov et al. | |
| 5,330,504 A | 7/1994 | Somerville et al. | |
| 5,331,966 A | 7/1994 | Bennett et al. | |
| 5,350,406 A | 9/1994 | Nitzsche et al. | |
| 5,360,436 A | 11/1994 | Alt et al. | |
| 5,366,487 A | 11/1994 | Adams et al. | |
| 5,379,776 A | 1/1995 | Murphy et al. | |
| 5,400,795 A | 3/1995 | Murphy et al. | |
| 5,404,880 A | 4/1995 | Throne | |
| 5,417,221 A | 5/1995 | Sickler | |
| 5,421,830 A | 6/1995 | Epstein et al. | |
| 5,447,519 A | 9/1995 | Peterson | |
| 5,447,524 A | 9/1995 | Alt | |
| 5,456,261 A | 10/1995 | Luczyk | |
| 5,458,623 A | 10/1995 | Lu et al. | |
| 5,462,060 A | 10/1995 | Jacobson et al. | |
| 5,464,433 A | 11/1995 | White et al. | |
| 5,497,780 A | 3/1996 | Zehender | |
| 5,513,644 A | 5/1996 | McClure et al. | |
| 5,527,347 A | 6/1996 | Shelton et al. | |
| 5,542,430 A | 8/1996 | Farrugia et al. | |
| 5,549,641 A | 8/1996 | Ayers et al. | |
| 5,549,654 A | 8/1996 | Powell | |
| 5,560,368 A * | 10/1996 | Berger | 600/517 |
| 5,560,369 A | 10/1996 | McClure et al. | |
| 5,605,159 A | 2/1997 | Smith et al. | |
| 5,609,158 A | 3/1997 | Chan | |
| 5,622,178 A | 4/1997 | Gilham | |
| 5,628,326 A | 5/1997 | Arand et al. | |
| 5,634,468 A * | 6/1997 | Platt et al. | 600/509 |
| 5,645,070 A | 7/1997 | Turcott | |
| 5,685,315 A | 11/1997 | McClure et al. | |
| 5,713,367 A | 2/1998 | Arnold et al. | |
| 5,718,242 A | 2/1998 | McClure et al. | |
| 5,730,142 A | 3/1998 | Sun et al. | |
| 5,738,105 A | 4/1998 | Kroll | |
| 5,749,900 A | 5/1998 | Schroeppel et al. | |
| 5,755,739 A | 5/1998 | Sun et al. | |
| 5,779,645 A * | 7/1998 | Olson et al. | 600/518 |
| 5,782,888 A | 7/1998 | Sun et al. | |
| 5,788,717 A | 8/1998 | Mann et al. | |
| 5,792,065 A | 8/1998 | Xue et al. | |
| 5,792,066 A | 8/1998 | Kwong | |
| 5,795,303 A | 8/1998 | Swanson et al. | |
| 5,797,399 A | 8/1998 | Morris et al. | |
| 5,817,133 A | 10/1998 | Houben | |
| 5,819,007 A | 10/1998 | Elghazzawi | |
| 5,827,197 A | 10/1998 | Bocek et al. | |
| 5,855,593 A | 1/1999 | Olson et al. | |
| 5,857,977 A | 1/1999 | Caswell et al. | |
| 5,873,897 A | 2/1999 | Armstrong et al. | |
| 5,944,744 A | 8/1999 | Paul et al. | |
| 5,951,484 A | 9/1999 | Hoium et al. | |
| 5,961,467 A | 10/1999 | Shimazu et al. | |
| 6,016,442 A | 1/2000 | Hsu et al. | |
| 6,091,990 A | 7/2000 | Hsu et al. | |
| 6,101,416 A | 8/2000 | Sloman | |
| 6,192,273 B1 | 2/2001 | Igel et al. | |
| 6,212,428 B1 | 4/2001 | Hsu et al. | |
| 6,223,078 B1 * | 4/2001 | Marcovecchio | 607/5 |
| 6,233,072 B1 | 5/2001 | Liu et al. | |
| 6,233,078 B1 | 5/2001 | Harano et al. | |
| 6,233,487 B1 | 5/2001 | Mika et al. | |
| 6,263,242 B1 | 7/2001 | Mika et al. | |
| 6,266,554 B1 | 7/2001 | Hsu et al. | |
| 6,275,732 B1 | 8/2001 | Hsu et al. | |
| 6,301,503 B1 | 10/2001 | Hsu et al. | |
| 6,308,095 B1 | 10/2001 | Hsu et al. | |
| 6,312,388 B1 | 11/2001 | Marcovecchio et al. | |
| 6,370,430 B1 | 4/2002 | Mika et al. | |
| 6,370,431 B1 * | 4/2002 | Stoop et al. | 607/14 |
| 6,430,435 B1 | 8/2002 | Hsu et al. | |
| 6,434,417 B1 | 8/2002 | Lovett | |
| 6,438,410 B2 | 8/2002 | Hsu et al. | |
| 6,449,503 B1 * | 9/2002 | Hsu | 600/518 |
| 6,456,871 B1 | 9/2002 | Hsu et al. | |
| 6,480,734 B1 | 11/2002 | Zhang et al. | |
| 6,484,055 B1 | 11/2002 | Marcovecchio | |
| 6,487,443 B2 | 11/2002 | Olson et al. | |
| 6,493,579 B1 | 12/2002 | Gilkerson et al. | |
| 6,516,225 B1 | 2/2003 | Florio | |
| 6,526,313 B2 | 2/2003 | Sweeney et al. | |
| 6,684,100 B1 | 1/2004 | Sweeney et al. | |
| 6,687,540 B2 | 2/2004 | Marcovecchio | |
| 6,708,058 B2 | 3/2004 | Kim et al. | |
| 6,728,572 B2 * | 4/2004 | Hsu et al. | 600/516 |
| 6,745,068 B2 | 6/2004 | Koyrakh et al. | |
| 6,760,615 B2 * | 7/2004 | Ferek-Petric | 600/518 |
| 6,766,190 B2 | 7/2004 | Ferek-Petric | |
| 6,889,081 B2 | 5/2005 | Hsu | |
| 6,978,177 B1 | 12/2005 | Chen et al. | |
| 7,031,764 B2 | 4/2006 | Schwartz et al. | |
| 7,039,463 B2 | 5/2006 | Marcovecchio | |
| 7,085,599 B2 * | 8/2006 | Kim et al. | 600/509 |
| 7,177,685 B2 | 2/2007 | Lincoln et al. | |
| 7,203,535 B1 | 4/2007 | Hsu et al. | |
| 7,212,849 B2 | 5/2007 | Zhang et al. | |
| 7,277,747 B2 | 10/2007 | Cazares et al. | |
| 7,289,845 B2 | 10/2007 | Sweeney et al. | |
| 7,415,307 B2 * | 8/2008 | Sharma et al. | 607/17 |
| 7,430,446 B2 | 9/2008 | Li | |
| 2002/0032469 A1 | 3/2002 | Marcovecchio | |
| 2002/0049474 A1 | 4/2002 | Marcovecchio et al. | |
| 2002/0087091 A1 | 7/2002 | Koyrakh et al. | |
| 2002/0091333 A1 | 7/2002 | Hsu et al. | |
| 2002/0183637 A1 | 12/2002 | Kim et al. | |
| 2002/0183639 A1 | 12/2002 | Sweeney et al. | |
| 2002/0198461 A1 | 12/2002 | Hsu et al. | |
| 2003/0060849 A1 | 3/2003 | Hsu | |
| 2003/0083586 A1 | 5/2003 | Ferek-Petric | |
| 2003/0083587 A1 | 5/2003 | Ferek-Petric | |
| 2003/0100923 A1 | 5/2003 | Bjorling et al. | |

| | | |
|---|---|---|
| 2003/0120316 A1* | 6/2003 | Spinelli et al. .......... 607/14 |
| 2003/0181818 A1 | 9/2003 | Kim et al. |
| 2004/0010200 A1 | 1/2004 | Sweeny et al. |
| 2004/0015090 A1 | 1/2004 | Sweeney et al. |
| 2004/0093035 A1 | 5/2004 | Schwartz et al. |
| 2004/0111119 A1 | 6/2004 | Sarkar et al. |
| 2004/0111120 A1 | 6/2004 | Sarkar et al. |
| 2004/0111121 A1 | 6/2004 | Brown et al. |
| 2004/0116972 A1 | 6/2004 | Marcovecchio |
| 2004/0127806 A1 | 7/2004 | Sweeney |
| 2004/0176694 A1 | 9/2004 | Kim et al. |
| 2004/0243014 A1 | 12/2004 | Lee et al. |
| 2005/0159781 A1 | 7/2005 | Hsu et al. |
| 2005/0256544 A1 | 11/2005 | Thompson |
| 2006/0074331 A1 | 4/2006 | Kim et al. |
| 2006/0079796 A1 | 4/2006 | Marcovecchio et al. |
| 2006/0095083 A1 | 5/2006 | Zhang et al. |
| 2006/0111643 A1 | 5/2006 | Cazares et al. |
| 2006/0122527 A1 | 6/2006 | Marcovecchio |
| 2006/0161069 A1 | 7/2006 | Li |
| 2006/0217621 A1 | 9/2006 | Kim et al. |
| 2006/0281998 A1 | 12/2006 | Li |
| 2006/0281999 A1 | 12/2006 | Li |
| 2007/0049974 A1 | 3/2007 | Li et al. |
| 2007/0142737 A1 | 6/2007 | Cazares et al. |
| 2007/0167849 A1 | 7/2007 | Zhang et al. |
| 2008/0140143 A1 | 6/2008 | Ettori et al. |

FOREIGN PATENT DOCUMENTS

| | | |
|---|---|---|
| EP | 0 469 817 A2 | 2/1992 |
| EP | 0469817 | 2/1992 |
| EP | 0 506 230 | 9/1992 |
| EP | 0506230 | 9/1992 |
| EP | 554208 | 8/1993 |
| EP | 0776630 | 11/1996 |
| EP | 0776631 | 11/1996 |
| EP | 0848965 | 6/1998 |
| JP | 06-090915 | 4/1994 |
| JP | 07-095967 | 4/1995 |
| WO | WO-97/39681 | 4/1996 |
| WO | WO-98/40010 | 9/1998 |
| WO | WO-98/53879 | 12/1998 |
| WO | WO-99/65570 | 12/1999 |
| WO | WO-00/10455 | 3/2000 |
| WO | WO-00/47278 | 8/2000 |
| WO | WO-0126733 A1 | 4/2001 |
| WO | WO-2006/049767 A1 | 5/2006 |
| WO | WO-2008/073266 A2 | 6/2008 |

OTHER PUBLICATIONS

Afonso, V. X., et al., "ECG Beat Detection Using Filter Banks", *IEEE Transactions on Biomedical Engineering*, 46(2), (Feb. 1999), 192-202.

Afonso, V. X., et al., "Filter Bank-based ECG Beat Classification", *Proceedings of the 19th Annual International Conference of the IEEE, Engineering in Medicine and Biology society*, (Oct. 30,-Nov. 2, 1997),97-100.

Afonso, V. X., et al., "Filter Bank-based ECG Beat Detection", *Proceedings of the 18th Annual International Conference of the IEEE Engineering in Medicine and Biology Society*, Amsterdam, The Netherlands,(1996),1037-1038.

Afonso, V. X., et al., "Filter Bank-based Processing of the Stress ECG", *IEEE 17th Annual Conference Engineering in Medicine and Biology Society*, 2, (Sep. 1995),887-888.

Afonso, V. X., et al., "Multirate Processing of the ECG using Filter Banks", *Computers in Cardiology*, (1996),245-248.

Duru, Firat , et al., "The Potential for Inappropriate Ventricular Tachycardia Confirmation Using the Intracardiac Electrogram (EGM) Width Criterion", *PACE*, vol. 22, 1999, (Jul. 1999),1039-1046.

Grady, Thomas A., et al., "Prognostice Significance of Exercise-Induced Left Bundle-Branch Block", *JAMA*, vol. 279, No. 2, Jan. 14, 1998, 153-156.

Kinoshita, Shinji , et al., "Transient Disappearance of Complete Right Bundle Branch (BBB) During Exercise", *Journal of Electrocardiology*, vol. 29, No. 3, 1996, 255-256.

Li, Dan , "Method and Apparatus for Rate-Dependent Morphology-Based Cardiac Arrhythmia Classification", U.S. Appl. No. 11/151,567, Filed on Jun. 13, 2005, 53 pgs.

Li, Dan , "Methods and Apparatuses for Cardiac Arrhythmia Classification Using Morphology Stability", U.S. Appl. No. 11/038,996, Filed Jan. 20, 2005, 74 pgs.

Morris, et al., "Intracardiac Electrogram Transformation: Morphometric Implications for Implantable Devices", *Journal of Electrocardiology, 29 Supplement*, (1996),pp. 124-129.

Stephany, et al., "Real-Time Estimation of Magnitude-Square Coherence for Use in Implantable Devices", *IEEE Computers in Cardiology*, (1992),pp. 375-378.

Thompson, Julie , "Template Based AV/VA Interval Comparison for the Discrimination of Cardiac Arrhytmia", U.S. Appl. No. 10/844,475, Filed May 12, 2004, 33 pgs.

Zhang, Yi , "Methods and Apparatuses for Arrhythmia Detection and Classification Using Wireless ECG", U.S. Appl. No. 10/975,166, Filed Oct. 28, 2004, 69 pgs.

"U.S. Appl. No. 09/248,800 Amendment Under 37 CFR 1.312 filed Jul. 17, 2001", 5 pgs.

"U.S. Appl. No. 09/248,800 Final Office Action mailed Dec. 22, 2000", 5 pgs.

"U.S. Appl. No. 09/248,800 Non Final Office Action mailed Mar. 29, 2000", 6 pgs.

"U.S. Appl. No. 09/248,800 Notice of Allowance mailed Apr. 17, 2001", 3 pgs.

"U.S. Appl. No. 09/248,800 Response filed Mar. 22, 2001 to Final Office Action mailed Dec. 22, 2000", 10 pgs.

"U.S. Appl. No. 09/248,800 Response filed Jun. 29, 2000 to Non Final Office Action mailed Mar. 29, 2000", 11 pgs.

"U.S. Appl. No. 09/249,128 Non Final Office Action mailed Aug. 16, 2000", 10 pgs.

"U.S. Appl. No. 09/249,128 Notice of Allowance mailed Feb. 2, 2001", 7 pgs.

"U.S. Appl. No. 09/249,128 Response filed Nov. 16, 2000 to Non Final Office Action mailed Aug. 16, 2000", 12 pgs.

"U.S. Appl. No. 09/352,056 Non Final Office Action mailed Sep. 25, 2001", 4 pgs.

"U.S. Appl. No. 09/352,056 Response filed Jan. 16, 2002 to Non Final Office Action mailed Sep. 25, 2001", 3 pgs.

"U.S. Appl. No. 09/352,056 Response filed Mar. 30, 2001 to Non Final Office Action mailed Dec. 5, 2000", 9 pgs.

"U.S. Appl. No. 09/352,056 Response filed Aug. 9, 2001 to Final Office Action mailed May 9, 2001", 4 pgs.

"U.S. Appl. No. 09/703,269 Non-Final Office Action mailed Jul. 1, 2003", 4 pgs.

"U.S. Appl. No. 09/703,269 Non-Final Office Action mailed Jun. 20, 2002", 3 pgs.

"U.S. Appl. No. 09/703,269 Response filed Mar. 31, 2003 to Non-Final Office Action mailed Nov. 29, 2002", 12 pgs.

"U.S. Appl. No. 09/703,269 Response filed Sep. 20, 2002 to Non-Final Office Action mailed Jun. 20, 2002", 3 pgs.

"U.S. Appl. No. 09/703,269, Non-Final Office Action mailed Nov. 29, 2002", 5 pgs.

"U.S. Appl. No. 09/703,269 Notice of Allowance mailed Sep. 8, 2003", 7 pgs.

"U.S. Appl. No. 09/848,605 Notice of Allowance mailed Apr. 2, 2002", 7 pgs.

"U.S. Appl. No. 10/014,933 Non Final Office Action mailed Nov. 14, 2003", 5 pgs.

"U.S. Appl. No. 10/014,933 Notice of Allowance mailed Feb. 6, 2004", 4 pgs.

"U.S. Appl. No. 10/014,933 Notice of Allowance mailed Apr. 22, 2005", 4 pgs.

"U.S. Appl. No. 10/014,933 Notice of Allowance mailed May 10, 2004", 4 pgs.

"U.S. Appl. No. 10/014,933 Response filed Jan. 16, 2004 to Non Final Office Action mailed Nov. 14, 2003", 10 pgs.

"U.S. Appl. No. 10/202,297 Amendment Under 37 CFR 1.312 mailed Feb. 2, 2005", 3 pgs.

"U.S. Appl. No. 10/202,297 Non Final Office Action mailed Dec. 31, 2003", 4 pgs.

"U.S. Appl. No. 10/202,297 Notice of Allowance mailed May 26, 2004", 4 pgs.

"U.S. Appl. No. 10/202,297 Notice of Allowance mailed Dec. 3, 2004", 4 pgs.

"U.S. Appl. No. 10/202,297 Response filed Mar. 19, 2004 to Non Final Office Action mailed Dec. 31, 2003", 10 pgs.

"U.S. Appl. No. 10/219,730 Non Final Office Action mailed Aug. 22, 2003", 8 pgs.

"U.S. Appl. No. 10/219,730 Notice of Allowance mailed Dec. 12, 2003", 8 pgs.

"U.S. Appl. No. 10/219,730 Response filed Nov. 3, 2003 to Non Final Office Action mailed Aug. 22, 2003", 15 pgs.

"U.S. Appl. No. 11/038,996, Response filed Nov. 26, 2007 to Non Final Office Action mailed Jul. 27, 2007", 11 pgs.

"U.S. Appl. No. 11/038,996, Response filed Apr. 16, 2008 to Final Office Action mailed Feb. 4, 2008", 8 pgs.

"U.S. Appl. No. 11/038,996, Non-Final Office Action mailed Jul. 27, 2007", 4 pgs.

"U.S. Appl. No. 11/038,996 Notice of Allowance mailed May 21, 2008", 6 pgs.

"U.S. Appl. No. 11/038,996 Final Office Action mailed Feb. 4, 2008", 7pgs.

"U.S. Appl. No. 11/151,567 Response filed Nov. 4, 2008 to Final Office Action mailed Sep. 5, 2008", 18 pgs.

"U.S. Appl. No. 11/151,567 Response filed Apr. 8, 2008 to Non-Final Office Action mailed Jan. 8, 2008", 16 pgs.

"U.S. Appl. No. 11/151,567 Non-Final Office Action mailed Jan. 8, 2008", 11 pgs.

"U.S. Appl. No. 11/151,567, Final Office Action mailed Sep. 5, 2008", 8 pgs.

"European Application Serial No. 1984963.7, Communication mailed Oct. 6, 2008", 4 pgs.

"International Application No. PCT/US2007/024975, Written Opinion mailed Jun. 27, 2008", 7 pgs.

Cazares, Shelley, et al., "Arrhythmia Discrimination Based on Determination of Rate Dependency", U.S. Appl. No. 11/312,280, Filed Dec. 20, 2005, 41 pgs.

* cited by examiner

CARDIAC RHYTHM MANAGEMENT SYSTEMS AND METHODS USING MULTIPLE MORPHOLOGY TEMPLATES FOR DISCRIMINATING BETWEEN RHYTHMS

CROSS REFERNCE TO RELATED APPLICATION(S)

This application is a continuation of U.S. patent application Ser. No. 10/291,200, filed on Nov. 8, 2002, now U.S. Pat. No. 7,031,764, the specification of which is incorporated herein by reference.

TECHNICAL FIELD

This document relates generally to medical systems, devices, and methods, and particularly, but not by way of limitation, to cardiac rhythm management systems and methods using multiple templates for discriminating between rhythms.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (i.e., a "surface ECG signal") obtained from electrodes placed on the patient's skin, or from electrodes implanted within the patient's body (i.e., an "electrogram signal"). The surface ECG and electrogram waveforms, for example, include artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poor spatial coordination of heart contractions. In either case, diminished blood circulation may result. For such patients, a cardiac rhythm management system may be used to improve the rhythm and/or spatial coordination of heart contractions. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular lead wire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency.

Cardiac rhythm management systems also include cardiac resynchronization therapy (CRT) devices for coordinating the spatial nature of heart depolarizations for improving pumping efficiency. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together.

Cardiac rhythm management systems also include defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac rhythm management systems also include devices that combine these functions, as well as monitors, drug delivery devices, and any other implantable or external systems or devices for diagnosing or treating the heart.

One problem faced by a cardiac rhythm management system treating certain ventricular tachyarrhythmias (VT), including ventricular fibrillation (VF), by a countershock, is in distinguishing such potentially dangerous arrhythmias from other heart rhythms, such as a supraventricular tachyarrhythmia (SVT), for which delivery of a responsive countershock is inappropriate, painful, and potentially risky. Some examples of such SVTs include atrial fibrillation (AF), atrial flutter, and sinus tachyarrhythmia.

One technique used in an implantable cardiac rhythm management device for discriminating between ventricular and supraventricular tachyarrhythmias compares the shape ("morphology") of each cardiac complex detected on an electrogram, during a period of high heart rate, to a template cardiac complex that was detected on the electrogram during normal sinus rhythm experienced by an inactive patient. A detected cardiac complex having a morphology similar to the template is deemed indicative of an SVT. A detected cardiac complex having a morphology different from the template is deemed indicative of a VT. However, the present inventors have recognized that this determination is confounded by the fact that some SVTs (e.g., "SVT with aberrancy") also have a morphology different from the template obtained during normal sinus rhythm of an inactive patient. As a result, using the above technique, such SVTs will instead be deemed indicative of VTs, resulting in the delivery of inappropriate countershocks. For these and other reasons, the present inventors have recognized that there exists an unmet need for improved techniques of discriminating between SVTs and VTs.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

This document discusses, among other things, systems, devices, and methods that will be described in applications involving implantable medical devices including, but not limited to, implantable cardiac rhythm management systems such as pacemakers, cardioverter/defibrillators, pacer/defibrillators, biventricular or other multi-site resynchronization or coordination devices, and drug delivery systems. However, these systems, devices, and methods may be employed in unimplanted devices, including, but not limited to, external pacemakers, cardioverter/defibrillators, pacer/defibrillators, biventricular or other multi-site resynchronization or coordination devices, monitors, programmers and recorders, whether such devices are used for providing a diagnostic, a therapy, or both a diagnostic and a therapy.

Figure 1:
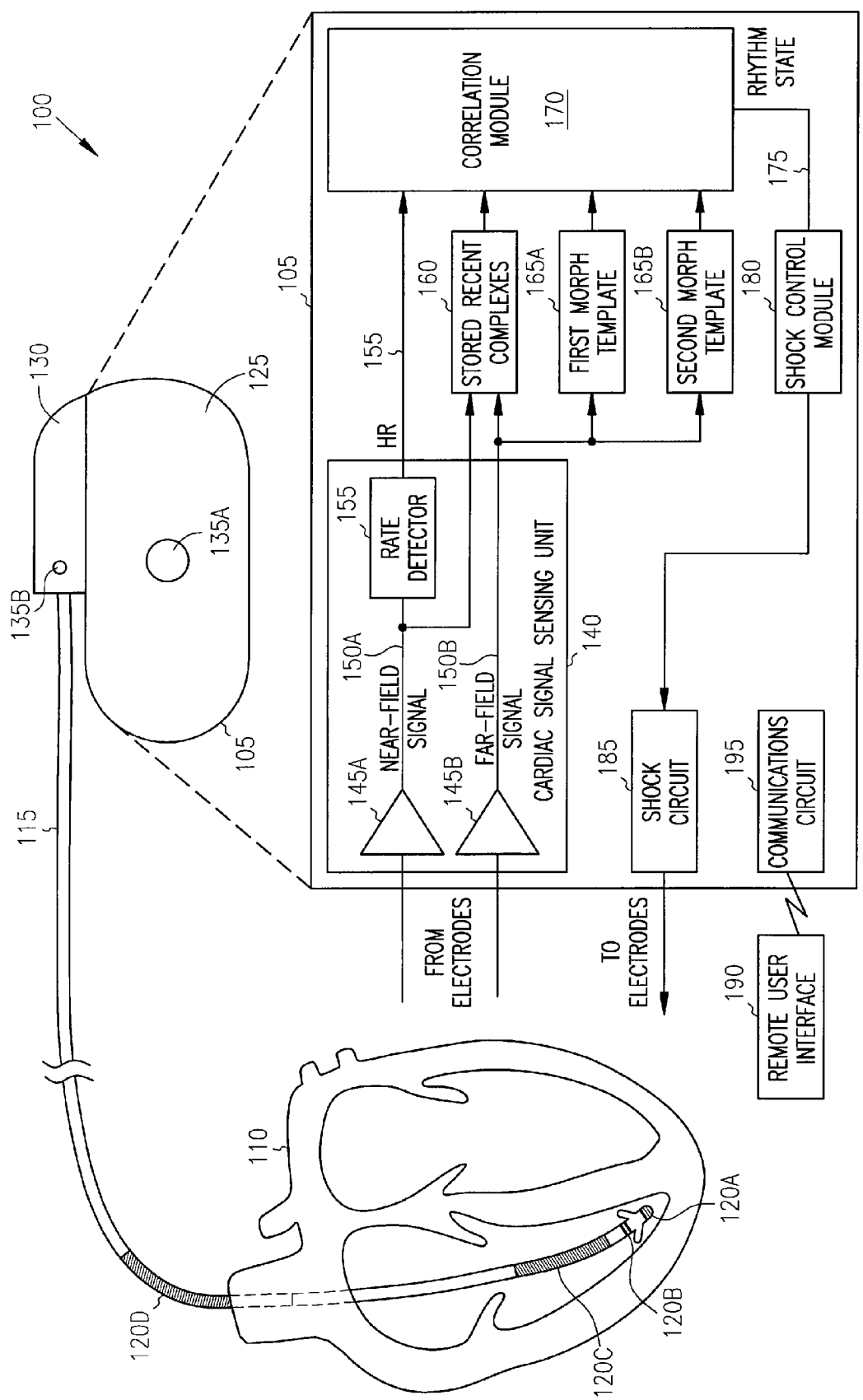
FIG. 1 is a schematic diagram illustrating generally, by way of example, but not by way of limitation, portions of a cardiac rhythm management system 100 using multiple morphology templates for discriminating between heart rhythms.

FIG. 1 is a schematic diagram illustrating generally, by way of example, but not by way of limitation, portions of a cardiac rhythm management system 100 using multiple morphology templates for discriminating between heart rhythms. In this example, system 100 includes an implantable cardiac rhythm management device 105 coupled to a heart 110 by one or more intravascular or other leadwires 115. Each leadwire 115 carries one or more electrodes sized and shaped to be disposed in or about heart 110, such as for sensing intrinsic cardiac signals from heart 110 and/or delivering electrical energy or other therapy to heart 110. The illustrative example of FIG. 1 includes a tip electrode 120A disposed at or near an apex of a right ventricle of heart 110, (optionally) a ring electrode 120B disposed slightly more proximally in the right ventricle, a shock electrode 120C disposed even more proximally in the right ventricle, and a superior vena cava (SVC) shock electrode 120D located in or near portions of the right atrium and superior vena cava of heart 110. Device 105 includes a hermetically-sealed case 125, such as for carrying electronic components therein, and a header 130 attached thereto, such as for receiving one or more leadwires 115. Device 105 may include additional electrodes, such as case electrode 135A and header electrode 135B, such as for unipolar sensing or therapy energy delivery.

In the illustrative example of FIG. 1, device 105 includes a cardiac signal sensing circuit 140. In this example, cardiac signal sensing circuit 140 includes a near-field sense amplifier 145A and a far-field sense amplifier 145B. In one example of a bipolar sensing configuration, near-field sense amplifier 145A is coupled to electrodes located relatively close to each other, such as electrodes 120A and 120C, for sensing a near-field cardiac signal; far-field sense amplifier 145B is coupled to electrodes located relatively farther from each other, such as electrodes 120C and 135A (or, alternatively, electrode 120C and the parallel combination of electrodes 120D and 135A), for sensing a far-field cardiac signal that includes information from a greater region of cardiac tissue. The resulting sensed near-field cardiac signal provided at node 150A typically includes relatively sharply defined cardiac complexes corresponding to intrinsic heart chamber depolarizations. Such relatively sharply defined cardiac complexes typically allow heart rate to be relatively easily discerned by rate detector 155, which provides an indication of the heart rate between sensed near-field cardiac complexes at node 155. The resulting cardiac complexes of the sensed far-field cardiac signal, provided at node 150B, typically exhibit some differences in morphology during different heart rhythms. Therefore, such differences in morphology of sensed far-field cardiac complexes are particularly useful for discriminating between different heart rhythms.

In FIG. 1, device 105 includes a buffer or other memory storage 160 for near-field and/or far-field data associated with recently-detected cardiac complexes. In this example, device 105 also includes memory storage for data associated with two or more morphological templates, such as a first morphological template 165A and for a second morphological template 165B, which are obtained from heart 110 under different conditions from each other, as explained further below. (Templates 165A-B may, in one example, be implemented entirely in software, such as by storing corresponding morphology-defining sets of morphological features). In the illustrated example, device 105 also includes a correlation module 170, which distinguishes between at least two different rhythm states by comparing and correlating the morphology of at least one recently received cardiac complex to at least one of the stored first and second morphological templates 165A-B. In certain examples, as explained below, correlation module 170 also uses the heart rate at node 155 in discriminating between different rhythm states.

An output of correlation module 170 provides, at node 175, an indication of the particular rhythm state, if any, obtained as a result of the comparison and correlation. In one example, correlation module 170 declares whether a detected arrhythmia is a supraventricular tachyarrhythmia (SVT) or a ventricular tachyarrhythmia (VT), and provides an indication of the same to shock control module 180. Shock control module 180 provides one or more triggering signals controlling delivery of a defibrillation countershock to heart 110 by shock circuit 185, such as a shock delivered between shock electrodes 120C-D, for example. In one example, shock control module 180 operates to inhibit delivery of a defibrillation shock if correlation module 170 declares an SVT, and operates to trigger delivery of a defibrillation shock if correlation module 170 declares a VT.

In the example of FIG. 1, system 100 also includes a programmer or other remote user interface 190, which is configured to be wirelessly communicatively coupled to a communication circuit 195 of device 105. In one example, remote user interface 190 allows a user to provide input information that is used in the distinguishing between heart rhythm states using multiple morphological templates. In another example, remote user interface 190 outputs information to the user relevant to the distinguishing between heart rhythm states using multiple morphological templates, by device 105.

Figure 2:
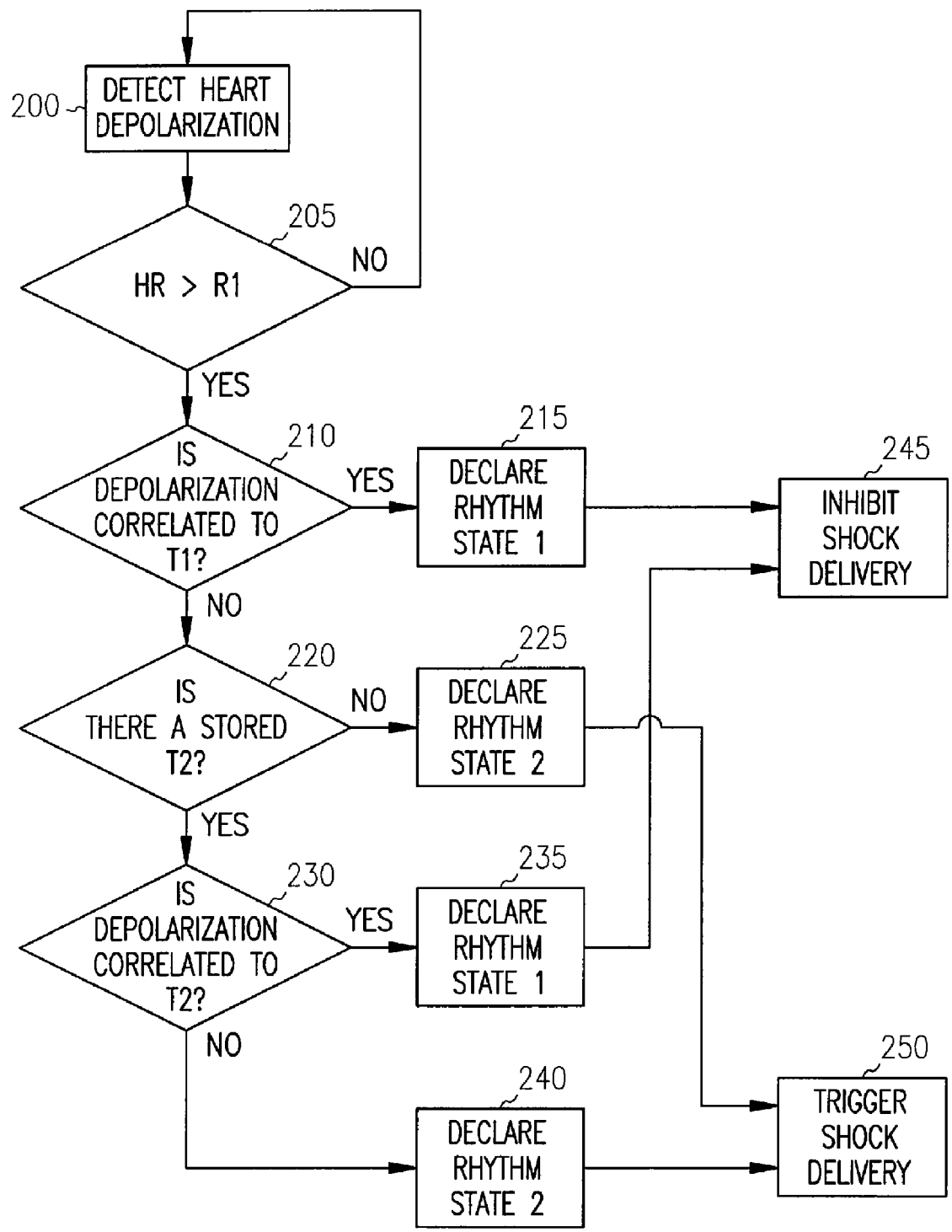
FIG. 2 is a flow chart illustrating generally, by way of example, but not by way of limitation, one method of distinguishing between heart rhythms using at least two morphological templates.

FIG. 2 is a flow chart illustrating generally, by way of example, but not by way of limitation, one method of distinguishing between heart rhythms using at least two morphological templates. In the example of FIG. 2, a heart depolarization is detected at 200, such as by sense amplifiers 145A and/or 145B. At 205, a heart rate, HR, is compared to a predetermined tachyarrhythmia rate threshold R1 (for an illustrative example, R1=145 beats per minute). HR>R1 indicates the presence of a tachyarrhythmia. HR≦R1 indicates the absence of a tachyarrhythmia. In one example, the heart rate used for the comparison is measured between the detected heart depolarization and an immediately preceding heart depolarization. In another example, an average heart rate over several successive pairs of heart depolarization is used instead.

If HR>R1, at 205, indicating the presence of a tachyarrhythmia, then a determination is made that further classifies the rhythm state, as described below. At 210, a morphology of the detected depolarization complex is compared to the first morphological template, T1, such as stored at 165A. In one example, this includes determining a degree of correlation between the morphologies of the detected complex and T1, comparing the degree of correlation to a predetermined threshold, and declaring a match if the correlation exceeds that predetermined threshold. In another example, this comparison includes correlating several (e.g., successive) detected depolarization morphologies to the first morphological template T1, and requiring that a predetermined percentage of the detected depolarizations be sufficiently correlated to T1 before a match is declared. In either case, if sufficient correlation exists to declare a match, then, at 215, a first rhythm state is declared.

Otherwise, at 220, a determination is made as to whether a second morphological template, T2, was previously stored at 165B. If no T2 has been stored, then, at 225, a second rhythm state is declared. Otherwise, at 230, a morphology of the detected depolarization complex is compared to the second morphological template, T2. In one example, this includes determining a degree of correlation between the morphologies of the detected complex and T2, comparing the degree of correlation to a predetermined threshold (which may be different than that for T1), and declaring a match if the correlation exceeds that predetermined threshold. In another example, this comparison includes correlating several (e.g., successive) detected depolarization morphologies to T2, and requiring that a predetermined percentage of the detected depolarizations be sufficiently correlated to T2 before a match is declared. In either case, if sufficient correlation exists at 230 to declare a match, then, at 235, a first rhythm state is declared. Otherwise, at 240, a second rhythm state is declared.

In a further example, the particular rhythm state obtained, as discussed above, is used as a control input affecting the delivery of electrical energy or other therapy to heart 110. In the example of FIG. 1, if the first rhythm state was declared at 215 or 235, then antitachyarrhythmia shock delivery is inhibited at 245. If the second rhythm state was declared at 225 or 240, then antitachyarrhythmia shock delivery is triggered at 250.

EXAMPLES OF MORPHOLOGICAL DISCRIMINATION BETWEEN RHYTHM STATES

Example 1

In a first example, first morphological template T1 corresponds to normal sinus rhythm obtained from a subject's heart 110 while the subject is resting or relatively inactive—and no tachyarrhythmia is present. Second morphological template T2 corresponds to normal sinus rhythm obtained from the subject's heart 110 while the subject is exercising or relatively active—and no ventricular tachyarrhythmia (VT) is present. For example, for acquiring and storing T2, the subject can be placed on a treadmill and an appropriate template depolarization complex acquired. In this example, a physician independently verifies (e.g., using a surface ECG and/or electrogram signals) that no VT was present during acquisition of T2. As an alternative to placing the subject on the treadmill, the physician may program device 105 to deliver atrial pacing pulses at a high rate, e.g., using an atrial leadwire; again, a physician verifies that no VT was present during this acquisition of T2.

Figure 3:
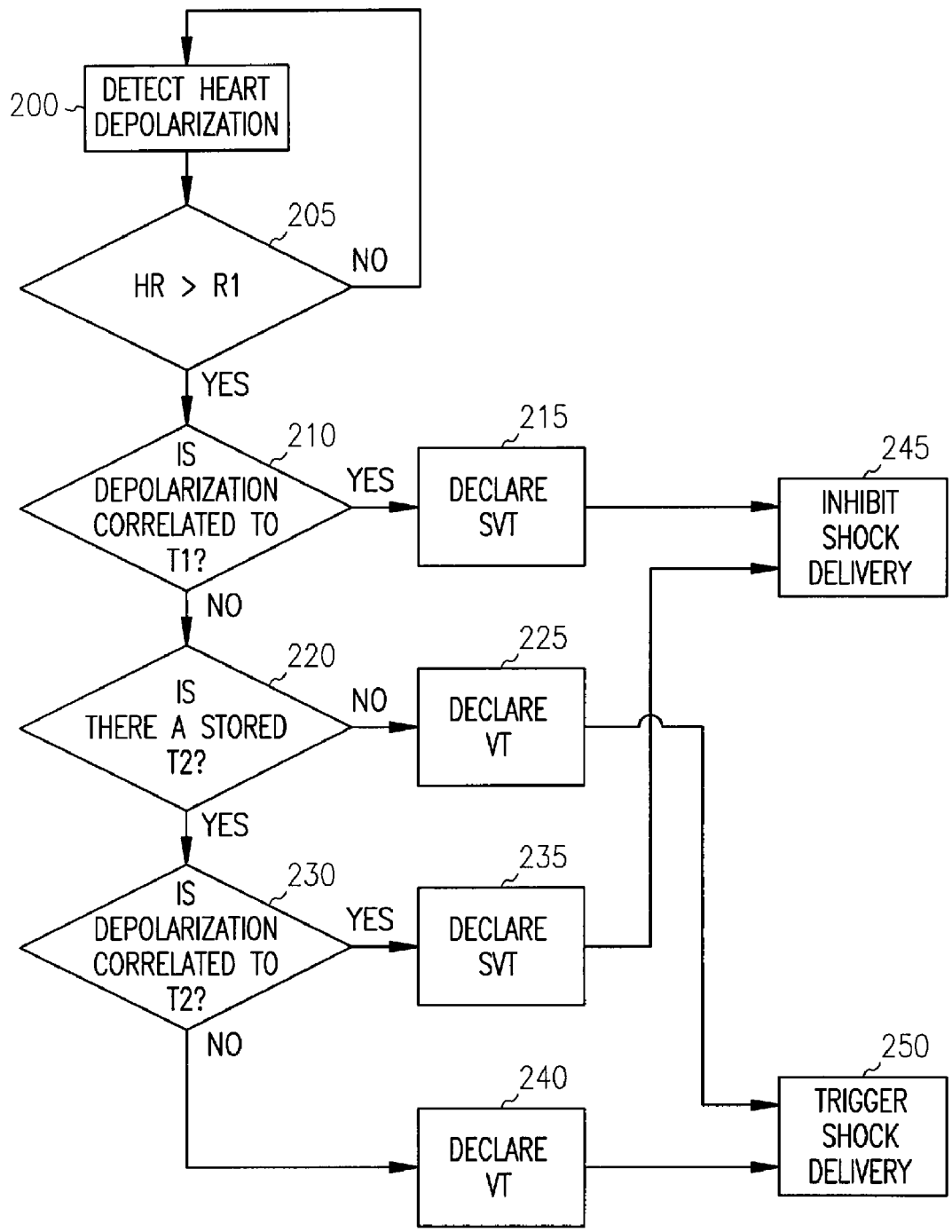
FIG. 3 is a flow chart illustrating generally, by way of example, but not by way of limitation, one method of distinguishing between supraventricular tachyarrhythmia (SVT) and ventricular tachyarrhythmia (VT) using at least two morphological templates.

In this example, as illustrated in the flow chart of FIG. 3, the first rhythm state is declared a supraventricular tachyarrhythmia (SVT), which results in inhibiting antitacharrhythmia shock delivery at 245, and the second rhythm state is declared a ventricular tachyarrhythmia (VT), which results in triggering antitachyarrhythmia shock delivery at 250. The present inventors have recognized that the use of a resting template T1 and an exercise template T2 accounts for morphological differences arising during exercise that are not indicative of VT. Using exercise template T2 adds another non-VT condition for which shock delivery is inhibited. This improves the specificity of delivering antitachyarrhythmia shock therapy for VTs, but not SVTs. For example, subjects experiencing left or right bundle branch block (BBB) induced during exercise will benefit from the additional specificity of using a morphological comparison of a detected depolarization complex to an exercise morphology template T2 as well as a resting morphology template T1. Similarly, other subjects experiencing left or right bundle branch block (BBB) mitigated during exercise will also benefit from the additional specificity of using a morphological comparison of a detected depolarization complex to an exercise morphology template T2 as well as a resting morphology template T1. These are merely illustrative examples of physiological conditions for which additional antitachyarrhythmia therapy delivery specificity is obtained; other physiological conditions exist that will also obtain increased specificity.

Example 2

In a second example, first morphological template T1 corresponds to normal sinus rhythm obtained from a subject's heart 110 while the subject is resting or relatively inactive, and no tachyarrhythmia is present. Second morphological template T2 corresponds to supraventricular tachyarrhythmia (SVT) rhythm obtained from the subject's heart 110 while no accompanying ventricular tachyarrhythmia (VT) is present. In one example, such an SVT may be induced by a physician in an electrophysiology (EP) lab; the physician independently verifies (e.g., using a surface ECG and/or electrogram signals) that no VT was present during acquisition of T2 during the SVT. In another example, such SVT template data is obtained from historical electrogram data obtained from the subject and stored by device 105; the physician independently verifies (e.g., using the stored electrogram signals) that no VT was present during acquisition of T2 during the stored SVT episode. Then, as discussed above with respect to FIG. 3, device 105 uses morphological comparisons of detected cardiac complexes to T1 and T2 to discriminate between SVT and VT, and adjust antitachyarrhythmia therapy delivery accordingly.

Example 3

Figure 4:
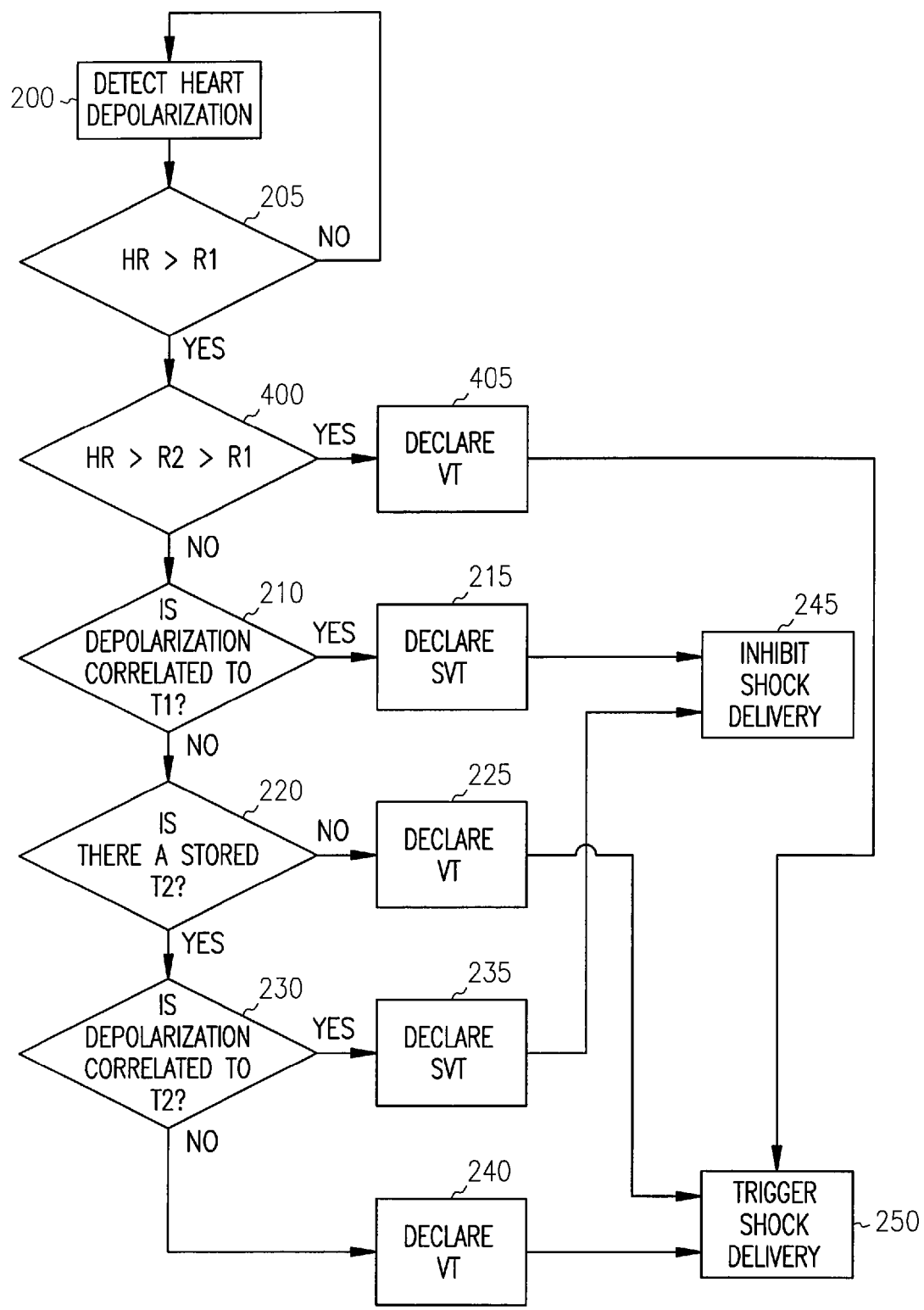
FIG. 4 is a flow chart illustrating generally, by way of example, but not by way of limitation, a method of distinguishing between heart rhythms using two heart rate thresholds and, if the detected heart rate is between the two rate thresholds, using at least two morphological templates.

In a third example, as illustrated in the flow chart of FIG. 4, the heart rate is compared to more than one threshold. In the example of FIG. 4, if the heart rate exceeds a first threshold R1 at 205, it is then compared at 400 to a second (higher) rate threshold R2 (for an illustrative example, R2=165 beats per minute). If, at 400, HR>R2, then, at 405, VT is declared. An antitachyarrhythmia shock is then triggered at 250. Otherwise if, at 400, R2>HR>R1, the process flow continues at 210 as discussed above with respect to FIGS. 2 and 3. In the example of FIG. 4, therefore, an extremely high detected rate triggers a declaration of VT and bypasses any comparison of a morphology of a detected depolarization complex to multiple morphological templates.

Example 4

Figure 5:
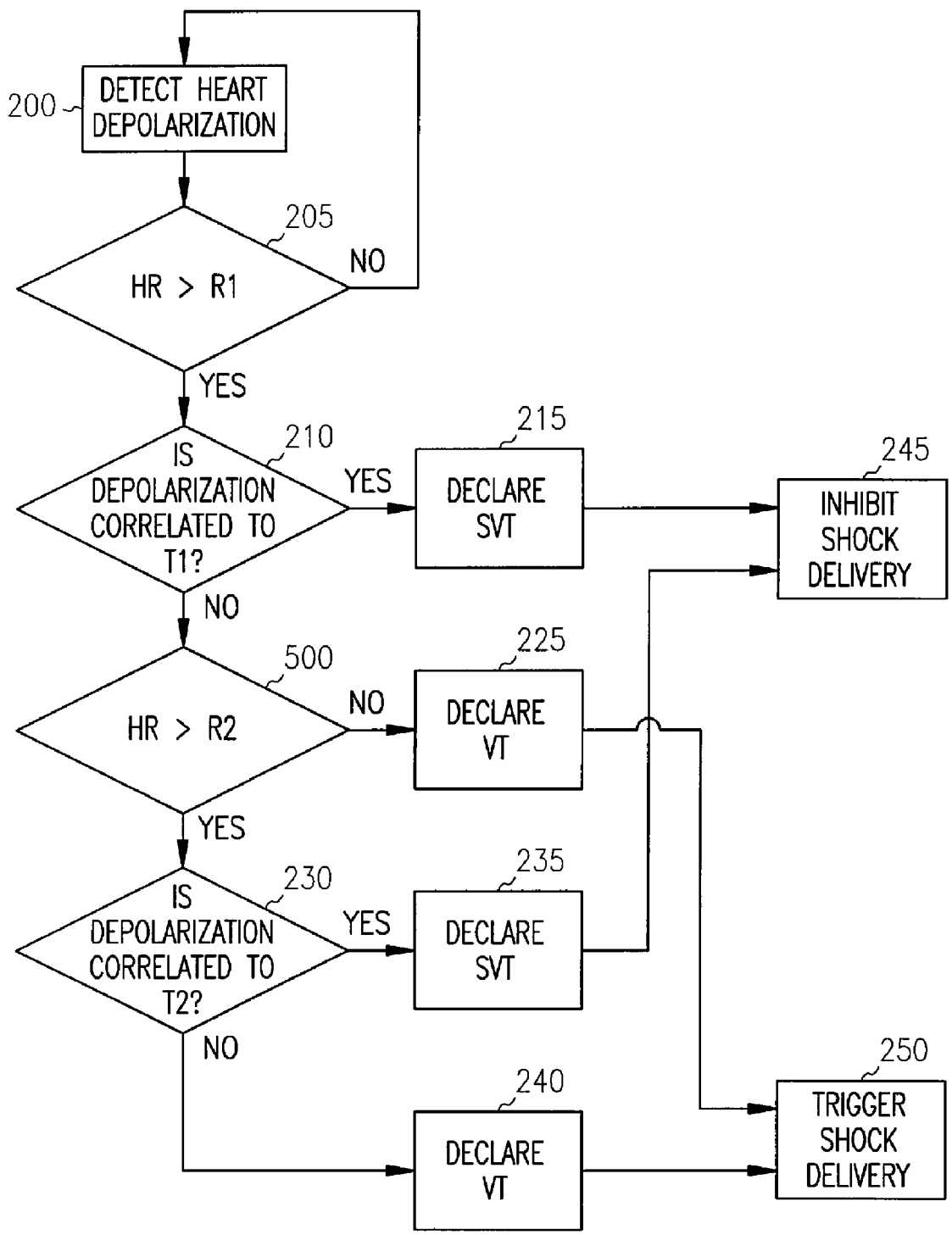
FIG. 5 is a flow chart illustrating generally, by way of example, but not by way of limitation, a method of distinguishing between heart rhythms by using two heart rate thresholds and, if the detected heart rate exceeds both rate thresholds, using at least two morphological templates.

In a fourth example, as illustrated in the flow chart of FIG. 5, the heart rate is used to determine whether a morphological comparison is made to more than one morphological template. In FIG. 5, if the depolarization is not correlated to T1 at 210, then at 500 the heart rate is compared to a second (higher) rate threshold R2 (for an illustrative example, R2=165 beats per minute). If, at 500, HR>R2, then a further comparison is made at 230 to T2, as discussed above with respect to FIGS. 2 and 3. Otherwise, if, at 500, R2>HR>R1, then, at 225, VT is declared, as discussed above with respect to FIGS. 2 and 3.

In all of the above examples, it is understood that morphological comparisons to more than two morphological templates (e.g., 3 templates, 4 templates) are also possible, and are included as additional embodiments of the systems, devices, and methods described in this document. In one such example, template T2 includes a plurality of multiple morphological templates to which a morphology comparison is made. Moreover, additional comparisons of heart rate to more than two threshold values are also possible and included as additional embodiments of the systems, devices, and methods described in this document. As a result, other embodiments may be capable of distinguishing between more than two different heart rhythm states (e.g., 3 heart rhythm states, 4 heart rhythm states, etc.), and accordingly adjusting therapy using such additional classification into several different rhythm states.

Also, because a particular subject's cardiac complex morphology may change over time (e.g., because of the effect of a drug being administered, or a change in the subject's heart condition), the multiple templates are typically updated occasionally or periodically. In one example, acquiring or updating a template is typically performed under the same or similar conditions to those conditions for which the correlation is performed. For example, where the templates T1 and T2 are differentiated by heart rate, in one example, device 105 uses rate detector 155 for automatically acquiring and/or updating the templates T1 and T2 under their corresponding heart rate conditions. In another example, however, device 105 uses a different sensor for acquiring and/or updating an "exercise template" T2, as discussed below.

EXAMPLES OF OPERATION OF THE CORRELATION MODULE

Figure 6:
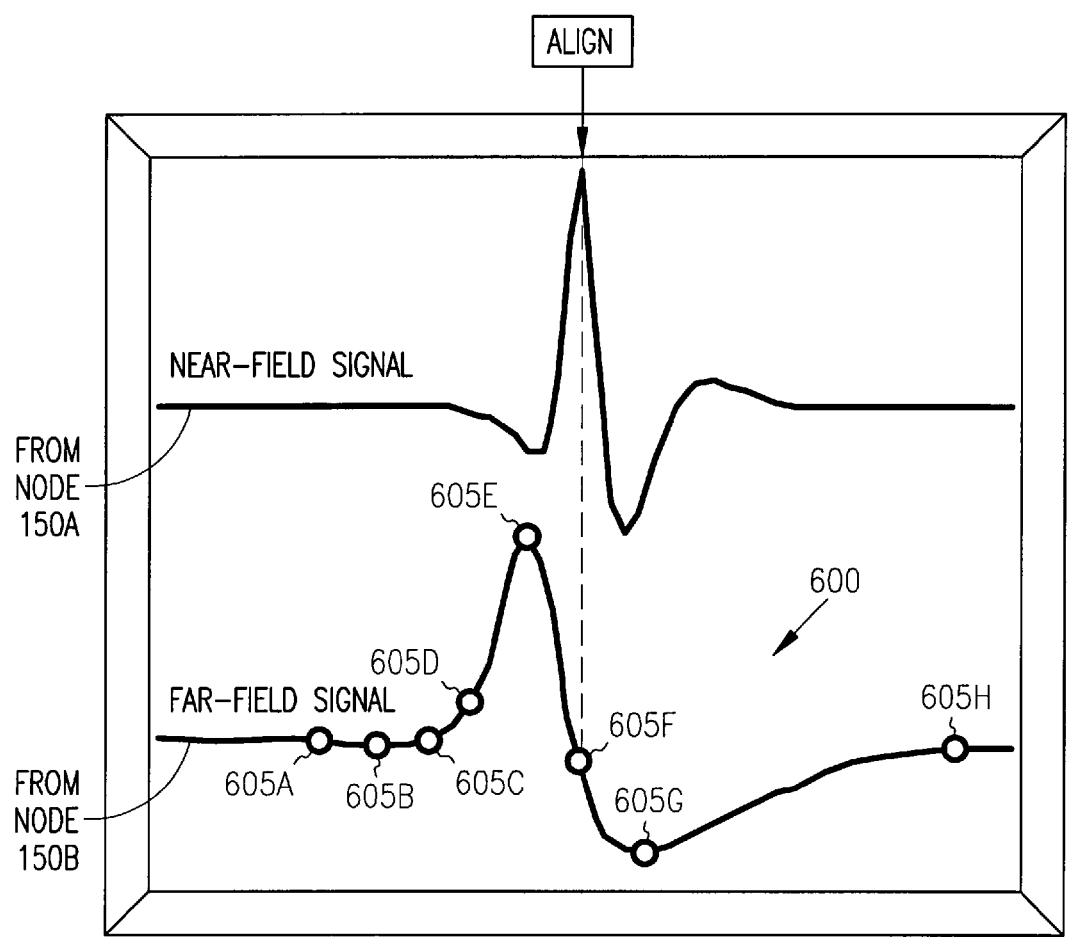
FIG. 6 is a signal diagram illustrating generally, by way of example, but not by way of limitation, a morphological template.
Figure 7:
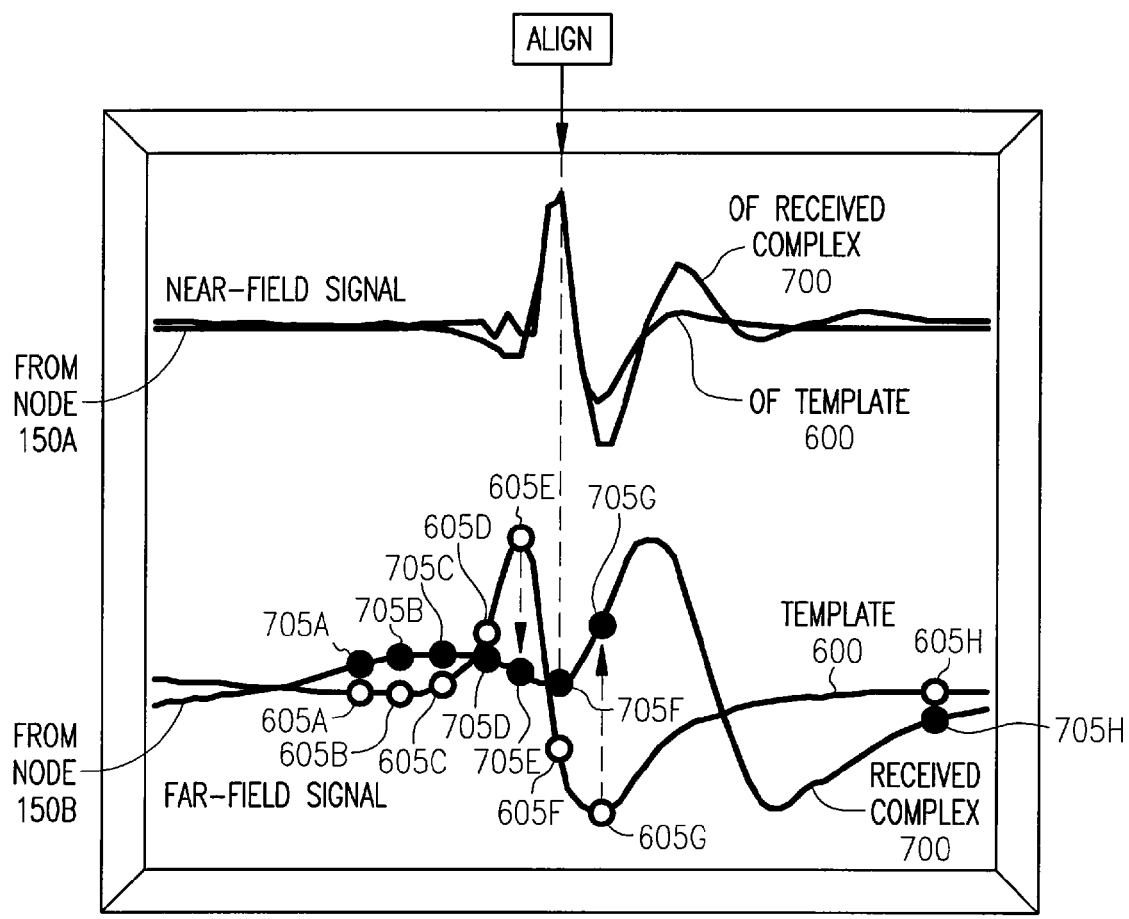
FIG. 7 is a signal diagram illustrating generally, by way of example, but not by way of limitation, comparison of a received complex to a morphological template, the received complex and the morphological template aligned by an alignment feature, such as an R-wave peak, of a near-field signal.

FIG. 6 is a signal diagram illustrating generally, by way of example, but not by way of limitation, one example of a morphological template 600, such as T1 or T2, obtained from the far-field signal at 150B. In this example, template 600 includes a collection of eight morphology-defining features 605A-H extracted from the far-field signal. In this example, an R-wave peak on a corresponding near-field signal at 150A, is used as an "alignment feature" of the template 600. Before the stored template 600 is later correlated to a received far-field cardiac complex, the point on the received far-field cardiac complex that aligns to its corresponding near-field R-wave peak (or other selected alignment feature) is used to "align" the received far-field cardiac complex to the template 600. More particularly, the template 600 is time-shifted such that the time coordinate of the R-wave peak of the near-field signal associated with the received far-field complex 700 being correlated to the template 600, as illustrated in the signal diagram of FIG. 7. Template 600 stores the times and amplitudes of each of the eight features 605A-H for comparison to a received far-field complex 700, such that the received far-field complex 700 can be classified into a rhythm state.

One illustrative example of the features 605A-H is disclosed in Jaeho Kim and et al. U.S. Pat. No. 6,889,079, entitled "METHOD AND SYSTEM FOR CHARACTERIZING SUPRAVENTRICULAR RHYTHM DURING CARDIAC PACING," which is incorporated herein by reference in its entirety, including its disclosure of obtaining eight features by first identifying five initial features, and then identifying three additional features determined at points between certain ones of the five initial features.

The received far-field cardiac complex 700 is sampled at the same times (relative to the alignment feature) as the features 605A-H in template 600, yielding comparison features 705A-H. In one example, correlation module 170 computes a feature correlation coefficient (FCC) using the amplitude ($x_i$) of each of the template features 605A-H and the amplitude ($y_i$) of the received far-field cardiac complex at these same times 705A-H relative to the alignment feature, as illustrated by Equation 1, below:

$$FCC = \frac{\left(8\sum_{i=1}^{8} x_i y_i - \left(\sum_{i=1}^{8} x_i\right)\left(\sum_{i=1}^{8} y_i\right)\right)^2}{\left(8\sum_{i=1}^{8} x_i^2 - \left(\sum_{i=1}^{8} x_i\right)^2\right)\left(8\sum_{i=1}^{8} y_i^2 - \left(\sum_{i=1}^{8} y_i\right)^2\right)} \quad (1)$$

In one example, the FCC computed in Equation 1 is compared to a predetermined threshold value to determine whether the received far-field cardiac complex 700 is correlated to the template 600. In one example, if this comparison indicates that the received complex 700 is uncorrelated to the template 600, then a second heart rhythm beat (e.g., VT beat) is declared. If 8 or more of the last 10 beats is uncorrelated, then correlation module 170 declares a second heart rhythm state (e.g., VT is declared). In one example, such correlation techniques are applied for comparison to both templates T1 and T2, such as at 210 and 230 of FIG. 2.

Other techniques for comparing received complexes to morphological templates can be substituted for the illustrative example discussed above. This document incorporates herein by reference the entire disclosure of Hsu et al. U.S. Pat. No. 6,308,095, entitled "SYSTEM AND METHOD FOR ARRHYTHMIA DISCRIMINATION," which is assigned to Cardiac Pacemakers, Inc., including incorporation of its disclosure of classifying cardiac complexes using morphological features. This document also incorporates herein by reference the entire disclosure of Marcoveccio U.S. Pat. No. 6,223,078, entitled "DISCRIMINATION OF SUPRAVENTRICULAR TACHYCARDIA AND VENTRICULAR TACHYCARDIA EVENTS," which is assigned to Cardiac Pacemakers, Inc., including incorporation of its disclosure of classifying cardiac complexes using morphological features. This document incorporates herein by reference the entire disclosure of Hsu et al. U.S. Pat. No. 6,275,732, entitled "MULTIPLE STAGE MORPHOLOGY-BASED SYSTEM DETECTING VENTRICULAR TACHYCARDIA AND SUPRAVENTRICULAR TACHYCARDIA," which is assigned to Cardiac Pacemakers, Inc., including incorporation of its disclosure of classifying cardiac complexes using morphological features. This document also incorporates herein by reference the entire disclosure of Marcoveccio U.S. Pat. No. 6,312,388, entitled "METHOD AND SYSTEM FOR VERIFYING THE INTEGRITY OF NORMAL SINUS RHYTHM TEMPLATES," which is assigned to Cardiac Pacemakers, Inc., including incorporation of its disclosure of classifying cardiac complexes using morphological features and updating templates. This document incorporates herein by reference the entire disclosure of Hsu et al. U.S. Pat. No. 6,266,554, entitled "SYSTEM AND METHOD FOR CLASSIFYING CARDIAC COMPLEXES," which is assigned to Cardiac Pacemakers, Inc., including incorporation of its disclosure of classifying cardiac complexes using morphological features. This document incorporates herein by reference the entire disclosure of Hsu et al. U.S. Pat. No. 6,449,503, entitled "CLASSIFICATION OF SUPRAVENTRICULAR AND VENTRICULAR CARDIAC RHYTHMS USING THE CROSS CHANNEL TIMING ALGORITHM," which is assigned to Cardiac Pacemakers, Inc., including incorporation of its disclosure of classifying cardiac complexes using morphological features. This document incorporates herein by reference the entire disclosure of Sweeney et al. U.S. Pat. No. 6,684,100, entitled "CURVATURE BASED METHOD FOR SELECTING FEATURES FROM AN ELECTRO-PHYSIOLOGIC SIGNALS FOR PURPOSE OF COMPLEX IDENTIFICATION AND CLASSIFICATION," which is assigned to Cardiac Pacemakers, Inc., including incorporation of its disclosure of classifying cardiac complexes using morphological features and curvatures. This document incorporates herein by reference the entire disclosure of Lovett U.S. Pat. No. 6,434,417, entitled "METHOD AND SYSTEM FOR DETECTING CARDIAC DEPOLARIZATION," which is assigned to Cardiac Pacemakers, Inc., including incorporation of its disclosure of classifying cardiac complexes using morphological features and frequency components. This document incorporates herein by reference the entire disclosure of Sweeney et al. U.S. Pat. No. 6,526,313, entitled "SYSTEM AND METHOD FOR CLASSIFYING CARDIAC DEPOLARIZATION COMPLEXES WITH MULTI-DIMENSIONAL CORRELATION," which is assigned to Cardiac Pacemakers, Inc., including incorporation of its disclosure of classifying cardiac complexes using morphological features and multidimensional correlation.

In the above discussion of FIGS. 1-7, the systems and methods utilized a heart rate (e.g., at node 155) that was represented as being obtained from a rate detector 155 that extracts heart rate from a near field signal obtained from cardiac electrodes. This heart rate was also used for comparing to various rate thresholds (see, e.g., 205 of FIG. 2, 400 of FIG. 4, etc.). However, obtaining heart rate from cardiac electrodes for distinguishing between heart rhythm states may, in certain conditions, be affected by the arrhythmias being distinguished, noisy cardiac signals, etc. Therefore, it may be desirable to either validate such sensed heart rate information obtained from an electrogram, or, alternatively, to use a different indication of heart rate.

Figure 8:
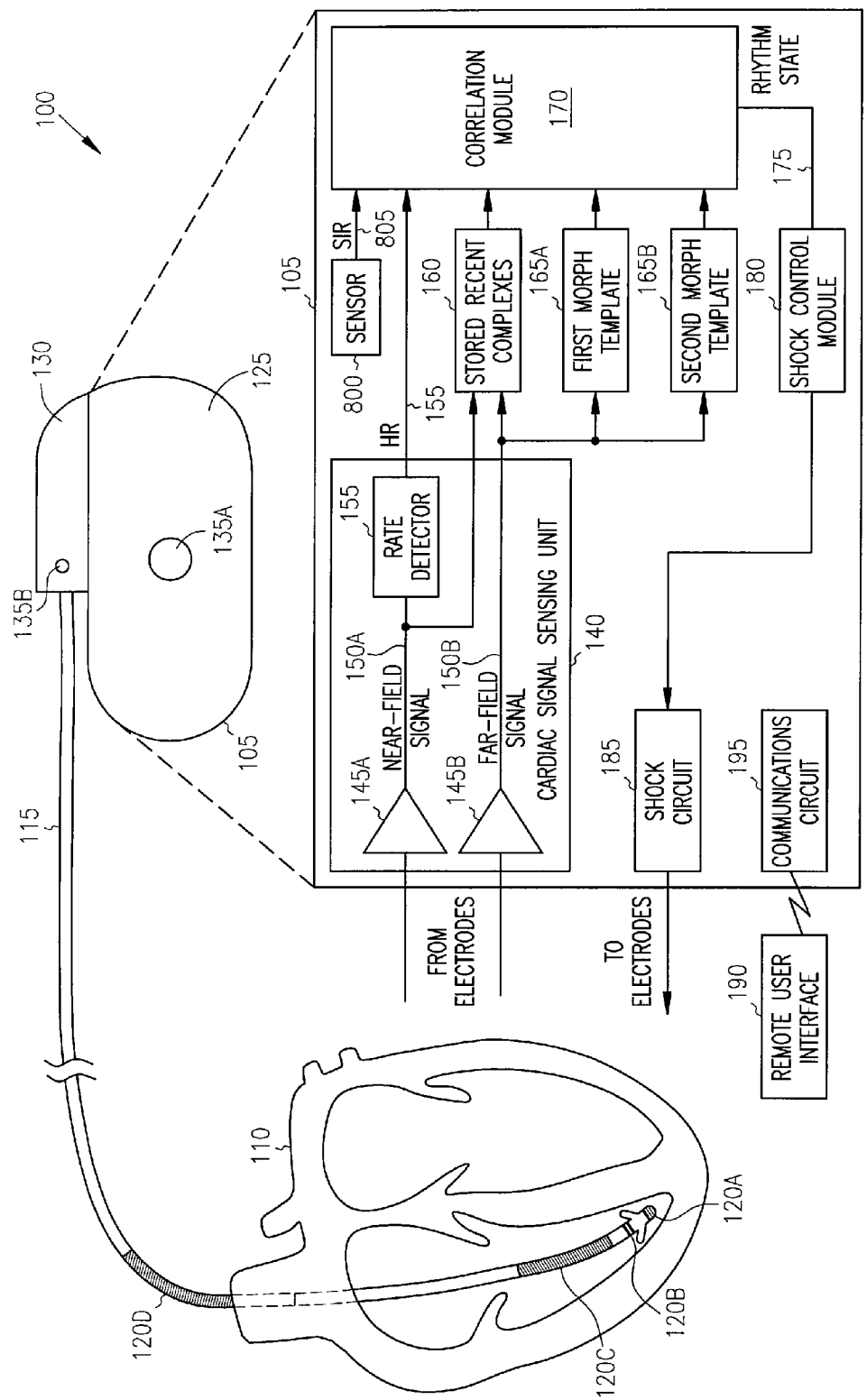
FIG. 8 is a schematic diagram illustrating generally, by way of example, but not by way of limitation, one embodiment of a system using at least one sensor.

FIG. 8 is a schematic diagram illustrating generally, by way of example, but not by way of limitation, one embodiment of a system 100 using at least one sensor 800. In the example of FIG. 8, sensor 800 may include an accelerometer, a minute ventilation sensor, or the like, providing an indication of patient activity. In one example, this indication of patient activity is provided as a sensor output (SO) at node/bus 802, to correlation module 170. The SO is positively correlated to a patient's activity (for an activity sensor) or metabolic need (for a metabolic need sensor); a larger value of SO corresponds to a higher activity level (or metabolic need). In a further example, the indication of patient activity is provided as a sensor-indicated rate (SIR), at node/bus 802, to correlation module 170. The SIR represents a computed heart rate deemed appropriate for the patient, based on activity and/or metabolic need information obtained from the SO of sensor 800. The SIR is also positively correlated to a patient's activity (for an activity sensor) or metabolic need (for a metabolic need sensor); a larger value of SIR corresponds to a higher activity level (or metabolic need). Numerous techniques known in the art (e.g., using rate-response curves) are available for mapping the SO to the SIR.

Figure 9:
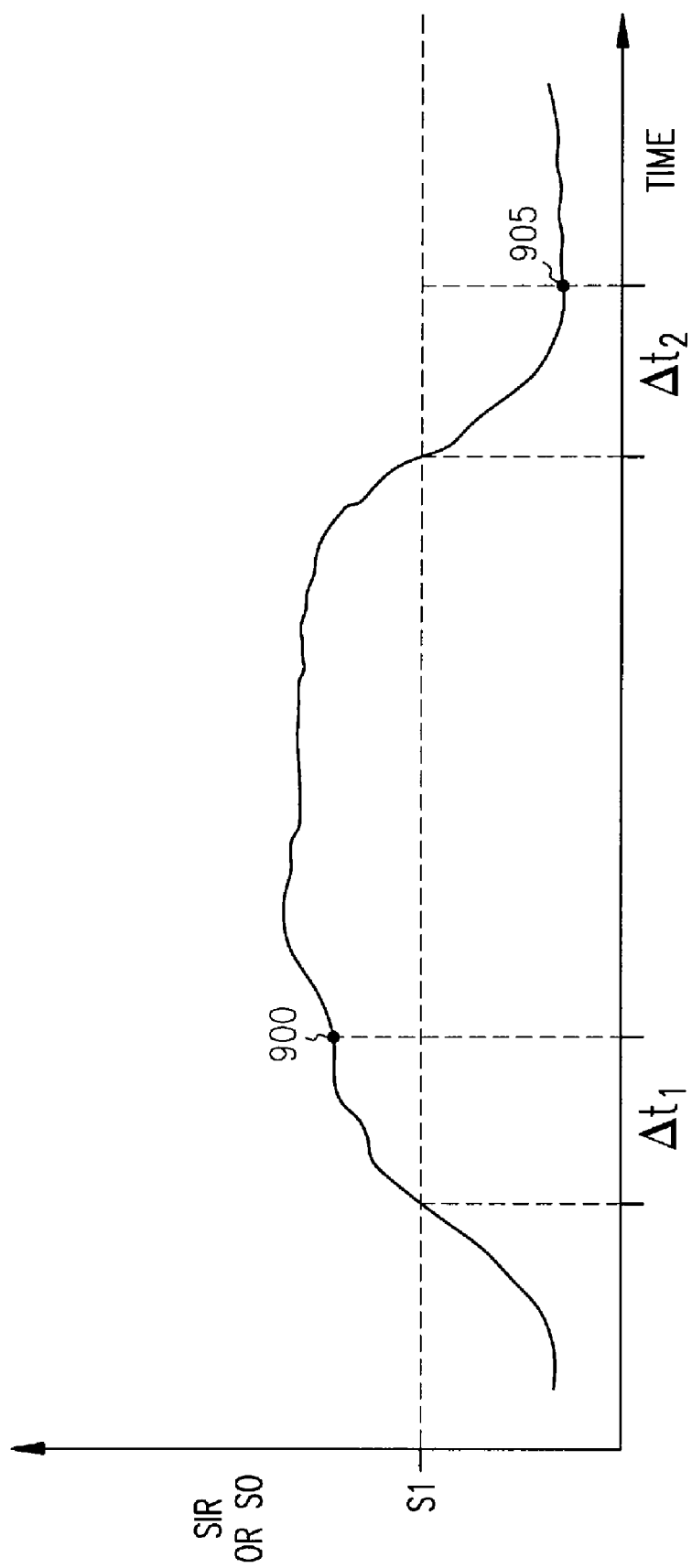
FIG. 9 is a graph of SIR (or SO) as a function of time, such as where SIR (or SO) is used in acquiring and/or updating an "exercise template" T2 and/or a "resting template" T1.

In one example, SIR (or SO) is used in acquiring and/or updating an "exercise template" T2 and/or a "resting template" T1, as illustrated generally in the graph of FIG. 9, which depicts SIR (or SO) as a function of time. In FIG. 9, the exercise template T2 is acquired (or updated) at point 900, after the SIR (or SO) has exceeded a corresponding exercise threshold S1 for a predetermined period of time Δt1. A resting template T1 is acquired (or updated) at point 905, after the SIR (or SO) has fallen below the corresponding exercise threshold S1 for a predetermined period of time Δt2. Alternatively, two different values of the activity threshold S1 (e.g., S1A and S1B) are used for triggering the respective time periods (Δt1 and Δt2) after which the respective exercise and resting templates are obtained. In another example, these two different values of the activity threshold (e.g., S1A and S1B) trigger the obtaining of the respective exercise and resting templates T2 and T1, without requiring the SIR or SO to be above or below such threshold values for a period of time.

Figure 10:
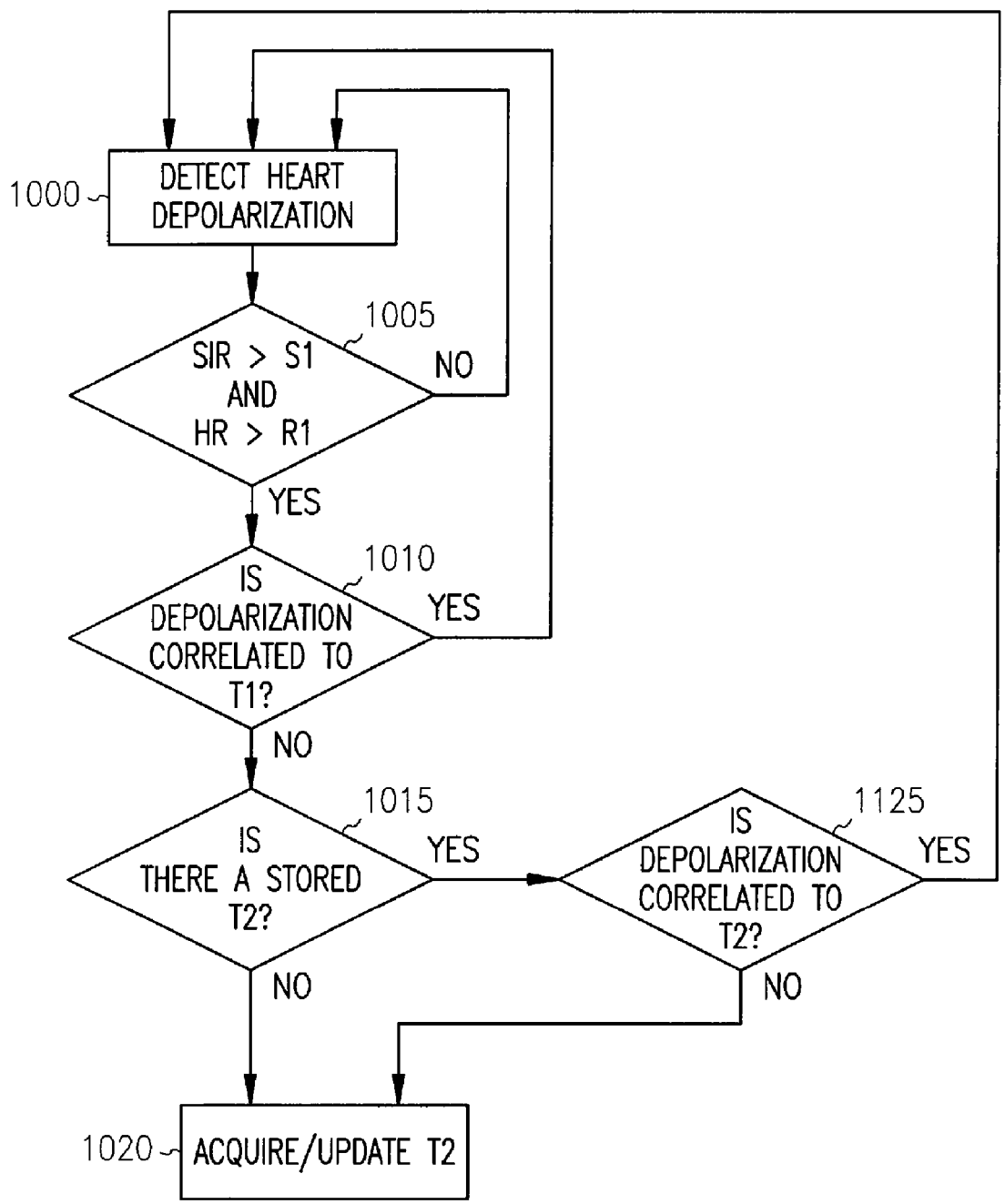
FIG. 10 is a flow chart illustrating generally one example in which, among other things, an exercise template T2 is acquired only if there is insufficient correlation to the resting template T1 during a period of exercise.

FIG. 10 is a flow chart illustrating generally one example in which, among other things, an exercise template T2 is acquired only if there is insufficient correlation to the resting template T1 during a period of exercise. In the example of FIG. 10, a heart depolarization is detected at 1000. At 1005, the SIR (or SO) and HR are monitored; if the SIR exceeds a predetermined threshold S1, and the HR exceeds a predetermined threshold R1, then at 1010 a determination is made as to whether the detected depolarization is sufficiently correlated to the resting template T1. If, at 1000, the detected depolarization is not sufficiently correlated to the resting template T1, and there is not a stored exercise template T2 at 1015, then at 1020, an exercise template T2 is acquired. At 1015, if there is not a stored exercise template T2, then at 1025 a determination is made as to whether the detected depolarization is sufficiently correlated to the existing exercise template T2. If not, then exercise template T2 is updated at 1020. In an alternative embodiment, multiple exercise templates T2 are acquired at 1020 if the depolarization is not sufficiently correlated to any of the existing exercise templates at 1025.

It is to be understood that the above description is intended to be illustrative, and not restrictive. For example, aspects of the above-discussed examples may be used in combination with each other. Many other embodiments will be apparent to those of skill in the art upon reviewing the above description. The scope of the invention should, therefore, be determined with reference to the appended claims, along with the full scope of equivalents to which such claims are entitled. Moreover, the terms "first," "second," "third," etc. are used merely as labels, and are not intended to impose numeric requirements on their objects.

What is claimed is:

1. A machine-readable medium including instructions that, when performed by a machine, cause the machine to:
   obtain a first reference morphological template from a subject's heart in the absence of an arrhythmia, while the subject is resting or inactive;
   obtain a second reference morphological template from the heart under a condition different from that of the first morphological template;
   obtain at least one current cardiac complex;
   determine a degree of correlation between the at least one cardiac complex and at least one of the first and second morphological templates; and
   declare one of first and second rhythm states at least in part using the determined degree of correlation.

2. The machine-readable medium of claim 1, further including instructions that cause the machine to determine whether to deliver or inhibit a shock to a heart at least in part using which of the first and second rhythm states was declared.

3. The machine-readable medium of claim 1, in which the instructions to obtain the second morphological template occur under a condition in which the subject manifests at least one activity indicator value that is higher than the at least one activity indicator value that occurred during the obtaining the first morphological template.

4. The machine-readable medium of claim 1, in which the instructions to obtain the second morphological template occur under a condition in which the subject manifests an arrhythmia.

5. The machine-readable medium of claim 4, in which the instructions to obtain the second morphological template occur under a condition in which the subject manifests an induced arrhythmia.

6. The machine-readable medium of claim 1, in which the instructions to obtain the second morphological template occur during high-rate atrial pacing.

7. The machine-readable medium of claim 1, in which the instructions to obtain the second morphological template occur during controlled physical exertion.

8. The machine-readable medium of claim 1, in which the instructions to obtain the second morphological template occur under a condition in which the subject manifests a supraventricular tachyarrhythmia.

9. The machine-readable medium of claim 1, further comprising instructions to recurrently update at least one of the first and second morphological templates.

10. The machine-readable medium of claim 8, in which the episode of the supraventricular tachyarrhythmia is obtained from historical electrogram data.

11. A method comprising:
   obtaining a first reference morphological template from a subject's heart in the absence of an arrhythmia, while the subject is resting or inactive;
   obtaining a second reference morphological template from the heart during high-rate atrial pacing;
   obtaining at least one current cardiac complex;
   determining a degree of correlation between the at least one cardiac complex and at least one of the first and second morphological templates; and
   declaring one of a first and second rhythm state at least in part using the determined degree of correlation.

12. The method of claim 11, further including determining whether to deliver or inhibit a shock to a heart at least in part using which of the first and second rhythm states was declared.

13. A method comprising:
   obtaining a first reference morphological template from a subject's heart in the absence of an arrhythmia, while the subject is resting or inactive;
   obtaining a second reference morphological template from the heart during exercise;
   obtaining at least one current cardiac complex;
   determining a degree of correlation between the at least one cardiac complex and at least one of the first and second morphological templates; and
   declaring one of a first and second rhythm state at least in part using the determined degree of correlation.

14. The method of claim 13, further including determining whether to deliver or inhibit a shock to a heart at least in part using which of the first and second rhythm states was declared.

15. A method comprising:
   obtaining a first reference morphological template from a subject's heart in the absence of an arrhythmia, while the subject is resting or inactive;

obtaining a second reference morphological template, in which the second template is obtained from historical electrogram data of an episode of supraventricular tachyarrhythmia;

obtaining at least one current cardiac complex;

determining a degree of correlation between the at least one cardiac complex and at least one of the first and second morphological templates; and declaring one of a first and second rhythm state at least in part using the determined degree of correlation.

16. The method of claim 15, further including determining whether to deliver or inhibit a shock to a heart at least in part using which of the first and second rhythm states was declared.

17. A system comprising:

an electrogram sensing circuit, configured to receive first and second intrinsic cardiac signals, the electrogram sensing circuit configured to provide cardiac complexes, each cardiac complex having a morphology, and an indication of heart rate obtained from the first intrinsic cardiac signal;

a sensor, including a sensor output indicative of activity or metabolic need of the subject;

a stored first reference morphological template, coupled to the electrogram sensing circuit, the stored first morphological template obtained from the heart in the absence of an arrhythmia while the subject is resting or inactive;

a stored second reference morphological template, coupled to the electrogram sensing circuit and the sensor, the stored second morphological template obtained from the heart under a different sensor output condition from that of the first morphological template;

a correlation module, coupled to the electrogram sensing circuit and the first and second morphological templates, the correlation module configured to declare an indication of one of a first and a second rhythm state, including discriminating between the first and second rhythm states using a comparison of a morphology of at least one current cardiac complex of the second intrinsic cardiac signal to at least one of the first and second morphological templates, the at least one of the first and second morphological templates selected using the indication of heart rate provided by the electrogram sensing circuit; and a template updating control module, coupled to the second morphological template and the correlation module, the template updating control module configured to provide an updated exercise template to the correlation module if: (a) a first exercise template is not available to the correlation module or (b) an available exercise template is insufficiently correlated to the at least one cardiac complex of the intrinsic cardiac signal.

18. The system of claim 17, further comprising:

a shock circuit, configured to be coupled to at least one electrode for delivering a shock to the heart; and a shock control module, coupled to the correlation module and the shock circuit, the shock control module configured to trigger a shock if the correlation module declares the indication of the second rhythm state, and the shock control module configured to inhibit a shock if the correlation module declares the indication of the first rhythm state.

19. The system of claim 17, further comprising:

a first electrode, sized and shaped for being implanted in or near a subject's heart, the first electrode configured for sensing a heart rate from cardiac complexes;

a second electrode, sized and shaped for being implanted in or near the heart, the second electrode configured for sensing a morphology of a cardiac complex.

20. A method comprising:

obtaining a first reference morphological template from a subject's heart in the absence of an arrhythmia, while the subject is resting or inactive;

obtaining a second reference morphological template from the heart under a condition different from that of the first morphological template;

obtaining at least one current cardiac complex;

determining a degree of correlation between the at least one cardiac complex and at least one of the first and second morphological templates;

declaring one of a first and second rhythm state at least in part using the determined degree of correlation; and updating the second morphological template if the cardiac complex is not sufficiently correlated to at least one of the first and second morphological templates.

21. A system comprising:

means for obtaining a first reference morphological template from a subject's heart in the absence of an arrhythmia, while the subject is resting or inactive;

means for obtaining a second reference morphological template from the heart under a condition different from that of the first morphological template;

means for obtaining at least one current cardiac complex;

means for determining a degree of correlation between the at least one cardiac complex and at least one of the first and second morphological templates;

means for declaring one of first and second rhythm states at least in part using the determined degree of correlation; and means for updating at least one of the first and second morphological templates.

* * * * *